Figure 1:
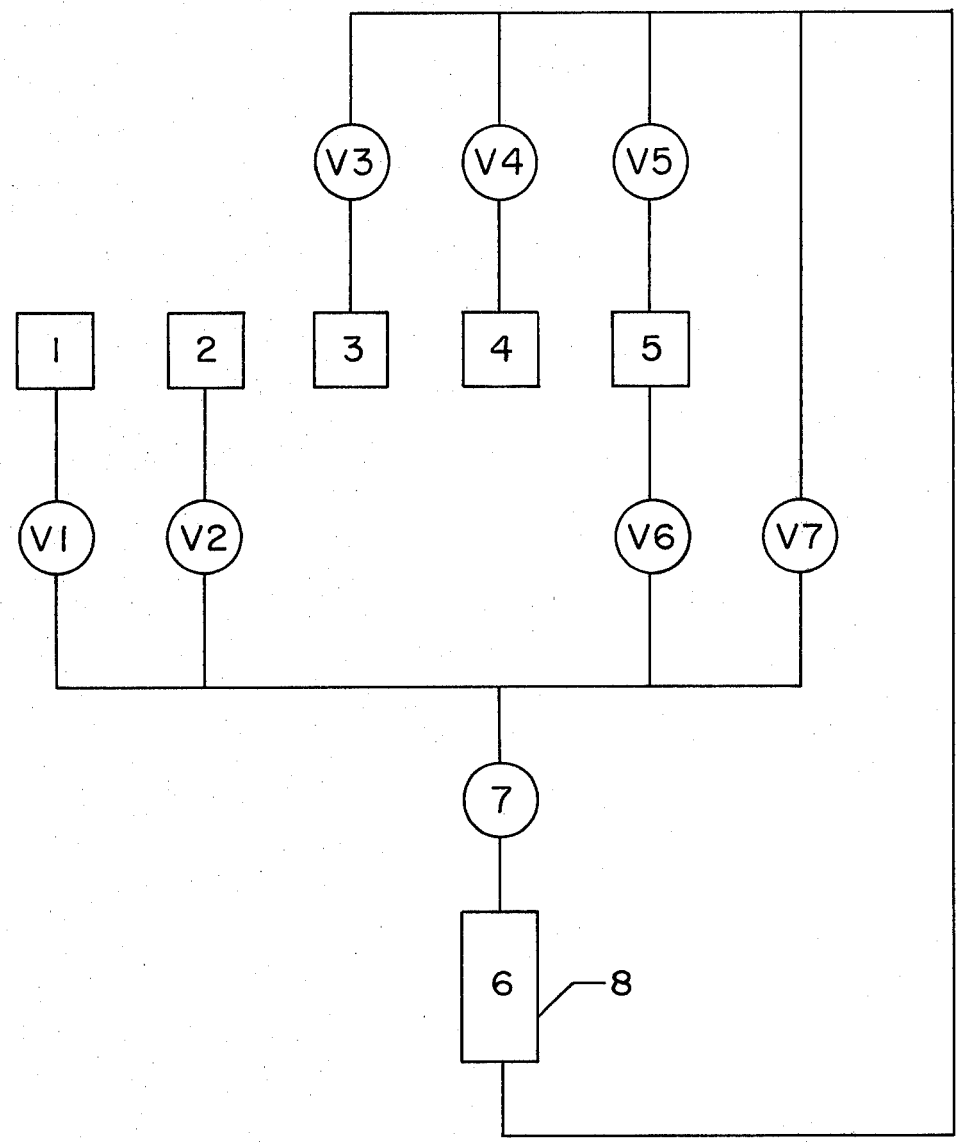

United States Patent [19]
Sutthoff et al.

[11] 4,022,637
[45] May 10, 1977

[54] METHOD FOR SEPARATION OF WATER SOLUBLE CARBOHYDRATES

[75] Inventors: Robert F. Sutthoff, Clinton; William J. Nelson, Camanche, both of Iowa

[73] Assignee: Standard Brands Incorporated, New York, N.Y.

[22] Filed: Feb. 23, 1976

[21] Appl. No.: 660,288

[52] U.S. Cl. .................... 127/46 A; 127/46 R; 210/31 C; 536/1

[51] Int. Cl.² ............... C07G 3/00; C13K 1/00; C13K 11/00

[58] Field of Search ......... 127/9, 46 R, 46 A, 46 B; 210/31 C; 536/1

[56] References Cited

UNITED STATES PATENTS

| | | | |
|---|---|---|---|
| 3,044,904 | 7/1962 | Serbia ....................... | 127/46 A |
| 3,044,905 | 7/1962 | Lefevre ..................... | 127/46 A |
| 3,044,906 | 7/1962 | Lefevre ..................... | 127/46 A |
| 3,184,334 | 5/1965 | Sargent ..................... | 127/46 A |
| 3,416,961 | 12/1968 | Mountfort ................. | 127/46 A |
| 3,483,031 | 12/1969 | Laver ........................ | 127/41 |

FOREIGN PATENTS OR APPLICATIONS

731,335   6/1955   United Kingdom

OTHER PUBLICATIONS

D. W. Simpson et al., Ind. Eng. Chem. 46(9), 1958–1962 (1954).
D. Gross, Int. Sugar Journal, 73 (874), 330–334 (1971).

*Primary Examiner*—Morris O. Wolk
*Assistant Examiner*—Sidney Marantz

[57] ABSTRACT

A method for the separation of water soluble carbohydrates from a feed solution by the utilization of a fractionation medium. The solution contains carbohydrates A and B in major amounts and carbohydrate A has a volume distribution coefficient at least 0.05 units greater than carbohydrate B when determined on said medium.

9 Claims, 2 Drawing Figures

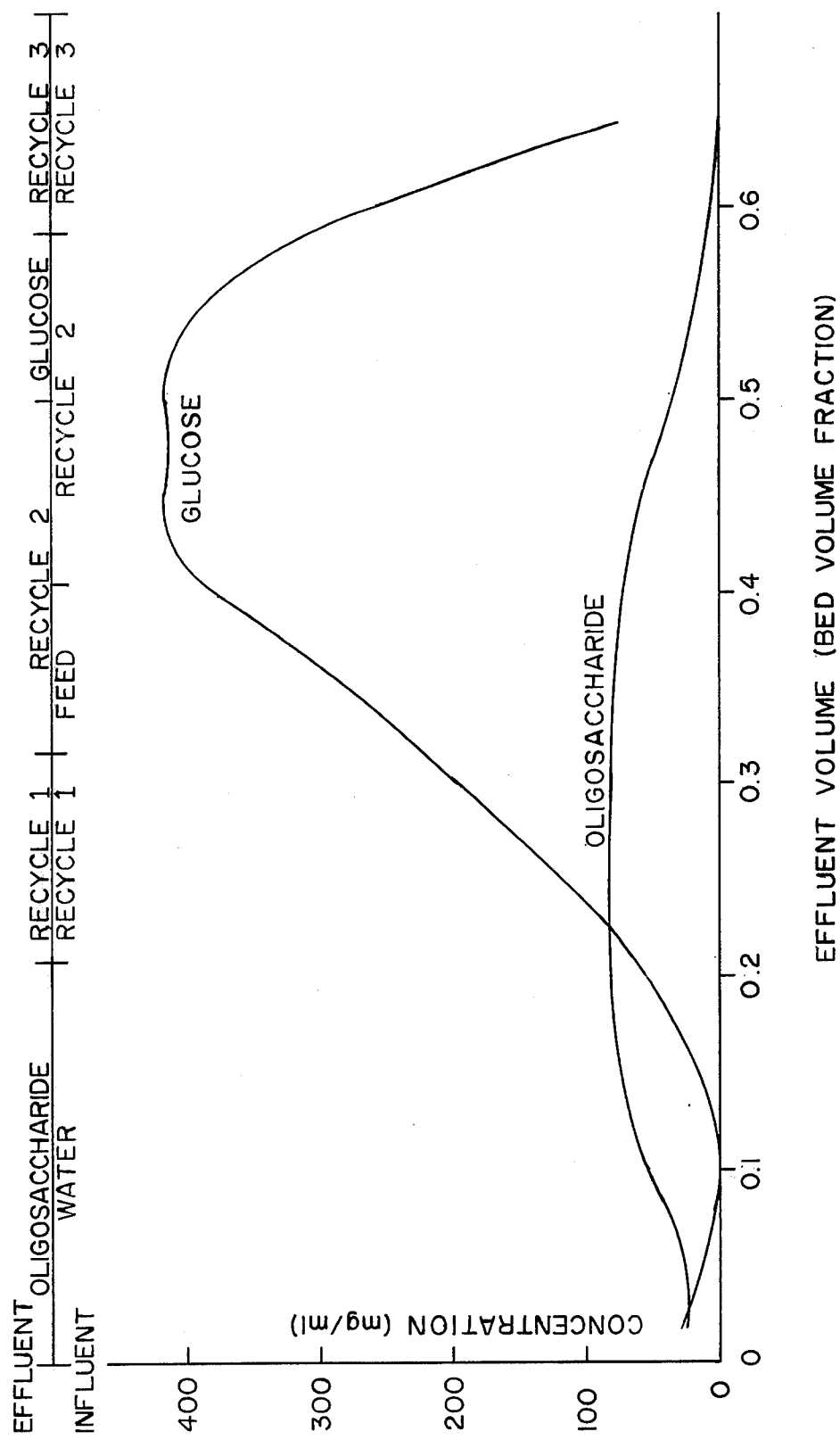
FIGURE II
FRACTIONATION OF GLUCOSE CONTAINING SOLUTION
DOWEX 50W-X4 (sodium)

METHOD FOR SEPARATION OF WATER SOLUBLE CARBOHYDRATES

BACKGROUND OF THE INVENTION

There are a number of publications and patents which disclose methods of separating water soluble carbohydrates and other materials. British Pat. No. 731,335 discloses the separation of a mixture of at least two water soluble organic compounds each having an ionization constant of not more than $1.4 \times 10^{-3}$. In this separation method, cation exchange resins which contain sulphonate radicals as the functional groups are utilized. U.S. Pat. No. 3,044,904 to Serbia and U.S. Pat. Nos. 3,044,905 and 3,044,906 both to Lefevre, disclose the utilization of various salts of a nuclearly sulfonated styrene resin to separate dextrose and fructose. In U.S. Pat. No. 3,184,334 to Sargent the separation of dextran from fructose by the utilization of ion exchange resins in the salt form and acid-and salt-forms is disclosed and U.S. Pat. No. 3,483,031 to Lauer et al. teaches the separation of glucose and fructose by using an ion exchange resin charged with calcium ions.

There are a numer of problems associated with the separation of various water soluble carbohydrates by the use of resins. Generally, large quantities of water are involved with such separations and, due to the dilution factors involved, removal of water to obtain the carbohydrates in a relatively pure and concentrated state requires high energy costs. Moreover, the equipment necessary to effect a efficient separation is generally quite complex and requires a number of holding tanks or similar devices and thereby entails a costly capital investment. Gross, *Intl. Sugar J.*, Vol 73, p. 330 (1971), discloses a partial solution to this problem whereby holding tanks, used for storage of recycle liquid, are eliminated by the utilization of two columns of resins positioned in series. However, this process does not result in the desired degree of separation.

OBJECTS

It is a principal object of the present invention to provide an efficient and economical method for separating carbohydrates from aqueous solutions which overcomes the problems heretofore encountered in such separations.

It is another object of the present invention to provide a effective method for separating carbohydrates wherein minimum amounts of water are utilized.

It is still another object of the present invention to provide a method for separating carbohydrates wherein only one recycle holding tank is necessary.

Other objects and advantages of this invention will be apparent from the following discussion and drawings.

SUMMARY OF THE INVENTION

This invention relates to a method for the separation of water soluble carbohydrates from a feed solution containing carbohydrates A and B in major amounts by the utilization of a fractionation medium. Carbohydrate A has a volume distribution coefficient at least 0.05 units greater than carbohydrate B when determined on said medium. The method comprises:

I. Admitting sequentially predetermined volumes of the feed solution and elution water to a column of the medium;

II. Separating the effluent from the column sequentially into the following fractions:
 a. carbohydrate A rich fraction,
 b. carbohydrate A rich fraction highly contaminated with carbohydrate B,
 c. carbohydrate B rich fraction highly contaminated with carbohydrate A,
 d. carbohydrate B rich fraction and
 e. dilute carbohydrate B rich fraction;

III. Admitting sequentially into the column:
 a. carbohydrate A rich fraction highly contaminated with carbohydrate B,
 b. a volume of feed solution approximately equal to the volume of carbohydrate B rich frction,
 c. carbohydrate B rich fraction highly contaminated with carbohydrate A,
 d. dilute carbohydrate B rich fraction and
 e. a volume of elution water approximately equal to the volume of the carbohydrate A rich fraction, the carbohydrate A rich fraction highly contaminated with carbohydrate B and the dilute carbohydrate B rich fraction being recycled directly to the column and the carbohydrate B rich fraction highly contaminated with carbohydrate A being collected while the feed solution is introduced into the column and then admitting said collected fraction into the column and IV. Repeating steps II and III in a cyclic manner.

DRAWINGS

FIG. 1 shows a diagrammatic arrangement of the method for the separation of carbohydrates from a water solution.

FIG. II graphically depicts the separation of glucose from other carbohydrates.

DESCRIPTION OF THE INVENTION

For purposes of the present invention, the volume distribution coefficient (D) is determined by the procedure of Olaf Samuelson, Methods in Carbohydrate Chemistry, VI, 1972, pp. 65–75, using the formula:

$$D = \frac{v}{x - y}$$

where $v$ is the retention volume (volume of effluent to attain peak maximum dry substance concentration), $x$ isthe volume of the fractionation medium and $y$ is the interstitial volume of the medium.

A number of types of fractionation media may be used in the method of the present invention so long as the volume distribution coefficients of the carbohydrates sought to be separated thereon differ by at least 0.05 units. Preferably, the volume coefficients will differ by at least 0.1 units and most preferably by at least 0.2 units.

THe preferred fractionation media are porous particulate ion exchange resins. In Table I, below, the volume distribution coefficients of various carbohydrates on a number of resins are illustrated:

TABLE I

| Volume Distribution Coefficients of Various Carbohydrates On Ion Exchange Resins | | | | | | | |
|---|---|---|---|---|---|---|---|
| Temperature °C | Ion Exchange Resin | Ionic Form | Xylose | Arabinose | Galactose | Dextrose | Fructose |
| 40 | Dowex 1-X8 | Bisulfite | | | | 1.49 | 0.95 |
| 40 | Dowex 1-X4 | Carbonate | 1.47 | 1.27 | 1.27 | | |
| 40 | Dowex 50W-X4 | Hydrazinium | 1.90 | 2.31 | 2.30 | 2.09 | 1.10 |
| 40 | Dowex 50W-X4 | Calcium | 1.15 | 1.35 | | | |
| 70 | Dowex 50W-X4 | Calcium | 1.07 | 1.21 | 1.11 | 1.00 | 1.22 |
| 40 | Dowex 50W-X4 | Strontium | 1.14 | 1.28 | | 1.05 | 1.33 |
| 70 | Dowex 50W-X4 | Strontium | 1.13 | 1.23 | 1.18 | | |

While the present method has application for the separation of a wide variety of carbohydrates, it is contemplated that it will be most applicable for the separation of fructose and glucose. Fructose-and glucose-containing solutions may be produced by processes well known in the art, such as the inversion of sucrose and the alkaline and enzymatic isomerization of glucose. Because of the low levels of impurities generally contained in enzymatically produced glucose-fructose solutions, such are preferred feed solutions in the present process. The presence of excessive quantities of impurities, such as saccharide degradation products, salts and the like, may decrease the effectiveness of the resin over extended periods of use.

The temperature, concentration of feed solution, height of column, particular fractionation medium utilized, number of recycles, volume of fractions and contact period all affect the efficiency of the separation.

The temperature at which separation is affected should not be so high as to cause breakdown of the carbohydrates and it must not be so low as to increase the viscosity of the solution to such a degree that the flow rate thereof through the column is deleteriously affected. In general, temperatures from about 40° to about 80° C provide satisfactory results.

The method of the present invention may be performed in an apparatus depicted in the diagrammatic arrangement shown in FIG. I. Components of the apparatus shown in FIG. I are identified as follows:
reservoir or source of feed solution 1,
reservoir or source of elution water 2,
holding tank 3 for carbohydrate A rich fraction,
holding tank 4 for carbohydrate B rich fraction,
storage tank 5 for recycle liquor,
vertical volumn 6 charged with a fractionation medium and fitted at the top thereof with a distributor for admitting solutions uniformly to the upper surface of the resin and at the bottom with a distributor for drawing off effluent fractions,
pump 7 for circulating various fractions,
heating means 8 for maintaining the temperature of the column of resin constant and
valves 1 to 7 for directing the flow of the various fractions to and from the column in accordance with the desired method of operation.

The following relationships must be satisfied to return recycle fractions directly to the column without storage.
1. Volume of feed solution = Volume of carbohydrate B rich fraction
2. Volume of elution water = Volume of carbohydrate A rich fraction
3. The volume of water which is initially displaced from the resin bed by the feed solutions prior to emergence of carbohydrate A plus the volume of carbohydrate A rich fraction must equal the cycle volume (total volume of carbohydrate A rich fraction, carbohydrate B rich fraction and recycle fractions). Note: The volume of water which is displaced from the resin will vary with different carbohydrates.

The volume of feed solution, elution water and recycle fractions can be varied within the constraints of the above relationships. Choice of volumes to satisfy the above stated equalities are identified below as predetermined.

At the start of the present process, column 6 is substantially full of a water-immersed resin. Valves 1 and 5 are opened and all other valves are closed. A predetermined volume of feed solution containing carbohydrates A and B is transferred from reservoir 1 through pump 7 to the top of column 6. The effluent from the column is directed through valve 5 and stored in tank 5. When the predetermined volume of feed liquor has been introduced via pump 7 to column 6 valve 1 is closed and valve 6 opened. The stored liquor in tank 5 is pumped to the column and the effluent continues to be directed to tank 5 for a predetermined volume. Valve 5 is then closed and valve 4 is opened. The remaining liquor in tank 5 is then pumped to the column while the carbohydrate B rich effluent is directed through valve 4 and collected in tank 4. The volume collected in tank 4 is about equal to the volume of feed liquor previously introduced. Valves 4 and 6 are then closed and valve 7 opened and the effluent rich in B but too dilute for use as product is recycled to the column directly. Valve 7 is then closed and valves 2 and 3 are opened. Elution water is introduced to column 6 and the carbohydrate A rich effluent liquor collected in tank 3. When the elution water has been introduced valves 2 and 3 are closed and valve 7 opened to recycle directly the liquor which is rich in carbohydrate A but too highly contaminated with carbohydrate B. After this recycling step the cycle is begun again by introducing feed liquor through valve 1 and storing the effluent which is rich in carbohydrate B, but highly contaminated with carbohydrate A in tank 5.

Since the dry substance concentration of the stored recycle fraction decreases during collection, the introduction of this fraction to the top of storage tank 5 will result in a layering effect which maintains the concentration gradient emerging from the column. Withdrawing this recycle fraction from the bottom of the tank allows the introduction of higher dry substance concentrations at the start of the recycle step.

The above described separation procedure may be performed continuously utilizing automatic sensing devices whereby the amounts of the various fractions are electronically determined so that valves depicted in the drawings are opened and closed according to a programmed sequence.

While the present method has been particularly described in regard to the separation of two carbohydrates, it should be understood that the separation process may be carried out so that an individual carbohydrate may be separated from a group of carbohydrates or that one group of carbohydrates may be separated from another group of carbohydrates.

EXAMPLE I

This example illustrates the separation of fructose and glucose from an enzymatically produced fructose-glucose containing solution.

A double-walled glass column having a 2.42 cm I.D. was filled with the calcium form of Dowex 50W-X4 cation exchange resin to a depth of 305 cm. The resin had a particle size of 35 to 70 U.S. Standard mesh. Water at 70° C was circulated through the column jacket to maintain the temperature of the resin at 68° C. An enzymatically produced fructose-glucose containing solution having a dry substance of 50 percent was fractionated on the resin column using a 10 ml/min flow rate in accordance with the method of the present invention. The sequence of collecting and recycling fractions shown in Table II below was repeated 12 times to approach equilibrium of the system.

TABLE II

Separation of Glucose and Fructose on Calcium Form of Cation Exchange Resin

| Influent | | Effluent | |
| --- | --- | --- | --- |
| Fraction | Volume (ml) | Fraction | Volume (ml) |
| Recycle I (glucose rich fraction highly contaminated with fructose) | 160 | glucose rich fraction | 328 |
| Feed (fructose containing solution) | 120 | Recycle I (glucose rich fraction highly contaminated with fructose) | 160 |
| Recycle II (fructose rich fraction highly contaminated with glucose) | 260 | Recycle II (fructose rich fraction highly contaminated with glucose) | 260 |
| Recycle III (dilute fructose rich fraction) | 160 | fructose rich fraction | 120 |
| Elution water | 328 | Recycle III (dilute fructose rich fraction) | 160 |

Recycles I and III were returned directly to the fractionation column. Recycle II was stored until the feed liquor was introduced into the column and then Recycle II was introduced into the column.

At the end of the 12cycle the carbohydrate content of the collected fractions and of the feed solution were determined and are set forth below:

TABLE III

| Fraction | Percent Dry Substance | Carbohydrates % | | |
| --- | --- | --- | --- | --- |
| | | Dextrose | Fructose | Other |
| Feed | 49.9 | 48.4 | 43.0 | 8.6 |
| Glucose rich fraction | 13.9 | 79.5 | 7.4 | 13.1 |
| Fructose rich fraction | 20.7 | 2.0 | 97.0 | 1.0 |

EXAMPLE II

This Example illustrates the separation of glucose from other carbohydrates in an enzymatically produced glucose containing solution.

A column of cation exchange resin described in Example I was prepared except that the resin volume was 1420 cm³.

An enzymatically produced glucose containing solution having a dry substance content of 53.5 percent was fractionated on the resin column using a 10 ml/min flow rate in accordance with the method of the present invention.

The separation sequence followed is set forth in Table IV below:

TABLE IV

Separation of Glucose and Oligosaccharides on Calcium Form of Cation Exchange Resin

| Influent | | Effluent | |
| --- | --- | --- | --- |
| Fraction | Volume (ml) | Fraction | Volume (ml) |
| Recycle I (oligosaccharide rich fraction highly contaminated with glucose) | 160 | Oligosaccharide rich fraction | 300 |
| Feed (glucose containing substrate) | 130 | Recycle I (oligosaccharide rich fraction highly contaminated with glucose | 150 |
| Recycle II (glucose rich fraction highly contaminated with oligosaccharides) | 250 | Recycle II (glucose rich fraction highly contaminated with oligosaccharides) | 250 |
| Recycle III (dilute glucose rich fraction) | 150 | Glucose rich fraction | 130 |
| Elution water | 300 | Recycle III (dilute glucose rich fraction) | 130 |

Recycles I and III were returned directly to the column. Recycle II was stored until the feed liquor had been introduced into the column. The sequence was repeated nineteen times to approach equilibrium of the system and then the carbohydrate content of the collected fractions and of the feed liquor were determined and are set forth in Table V below:

TABLE V

| Fraction | Percent Dry Substance | Carbohydrates % | |
|---|---|---|---|
| | | Glucose | Oligosaccharides |
| Feed | 53.5 | 79.5 | 19.8 |
| Oligosaccharide rich fraction | 6.3 | 22.9 | 76.4 |
| Glucose rich fraction | 35.6 | 95.4 | 3.7 |

In FIG. II, a graph is set forth relating effluent volumes at equilibrium to the concentration of glucose and oligosaccharides. The relative slope and dispositions of the oligosaccharide and glucose curves are constant under these conditions.

What is claimed is:

1. A method for the separation of water soluble carbohydrates from a feed solution by the utilization of a fractionation medium wherein the solution contains carbohydrates A and B in major amounts and carbohydrate A has a volume distribution coefficient of at least 0.05 units greater than carbohydrate B when determined on said medium comprising:
   I. Sequentially admitting predetermined volumes of the feed solution and elution water to a column of said medium;
   II. Separating the effluent from the column sequentially into the following fractions:
      a. carbohydrate A rich fraction,
      b. carbohydrate A rich fraction highly contaminated with carbohydrate B,
      c. carbohydrate B rich fraction highly contaminated with carbohydrate A,
      d. carbohydrate B rich fraction, and
      e. dilute carbohydrate B rich fraction,
   III. Admitting sequentially into the column:
      a. carbohydrate A rich fraction highly contaminated with carbohydrate B,
      b. a volume of feed solution approximately equal to carbohydrate B rich fraction,
      c. carbohydrate B rich fraction highly contaminated with carbohydrate A,
      d. dilute carbohydrate B rich fraction,
      e. a volume of elution water approximately equal to the volume of the carbohydrate A rich frction, the carbohydrate A rich fraction highly contaminated with carbohydrate B and the dilute carbohydrate B rich fraction being recycled directly to the column and the carbohydrate B rich fraction highly contaminated with carbohydrate A being collected while the feed solution is introduced into the column and then admitting said collected fraction into the column, and
   IV. Repeating steps II and III in a cyclic manner.

2. A method for the separation of water soluble carbohydrates as defined in claim 1, wherein carbohydrate A has a volume distribution coefficient of at least 0.1 units greater than carbohydrate B when determined on the medium.

3. A method for the separation of water soluble carbohydrates as defined in claim 2, wherein carbohydrate A has a volume distribution coefficient of at least 0.2 units greater than carbohydrate B when determined on the medium.

4. A method for the separation of water soluble carbohydrates as defined in claim 2, wherein the medium comprises porous particulate ion exchange resins.

5. A method for the separation of water soluble carbohydrates as defined in claim 2, wherein carbohydrate A is glucose and carbohydrate B is fructose.

6. A method for the separation of water soluble carbohydrates as defined in claim 4, wherein carbohydrate A is glucose and carbohydrate B is fructose.

7. A method for the separation of water soluble carbohydrates as defined in claim 6, wherein the column of said fractionation medium is maintained at a temperature of from about 40° to about 80° C.

8. A method for the separation of water soluble carbohydrates as defined in claim 7, wherein the carbohydrate B rich fraction highly contaminated with carbohydrate A is collected in a storage tank by directing said fraction into the top of said tank, and withdrawing said fraction from the bottom of said tank thereby maintaining the dry substance concentration gradient of said fraction.

9. A method for the separation of water soluble carbohydrates as defined in claim 8, wherein carbohydrate A is glucose and carbohydrate B is fructose.

* * * * *